United States Patent
Bouloussa et al.

(10) Patent No.: US 8,475,782 B2
(45) Date of Patent: Jul. 2, 2013

(54) METHOD FOR TREATING SURFACES WITH COPOLYMERS

(75) Inventors: Othman Bouloussa, Rueil Malmaison (FR); Vincent Semetey, Le Mans (FR); Francis Rondelez, Fontenay-Aux Roses (FR)

(73) Assignees: Institut Curie, Paris (FR); Centre National de la Recherche Scientifique, Paris (FR); Universite Pierre et Marie Curie (Paris IV), Paris (FR)

( * ) Notice: Subject to any disclaimer, the term of this patent is extended or adjusted under 35 U.S.C. 154(b) by 1347 days.

(21) Appl. No.: 11/885,283

(22) PCT Filed: Mar. 29, 2006

(86) PCT No.: PCT/IB2006/050951
§ 371 (c)(1), (2), (4) Date: Dec. 13, 2007

(87) PCT Pub. No.: WO2006/103631
PCT Pub. Date: Oct. 5, 2006

(65) Prior Publication Data
US 2008/0226585 A1  Sep. 18, 2008

(30) Foreign Application Priority Data
Mar. 31, 2005 (EP) .................................. 05007026

(51) Int. Cl.
*A61K 31/00* (2006.01)
*A61K 31/74* (2006.01)

(52) U.S. Cl.
USPC .................................... 424/78.32; 424/78.08

(58) Field of Classification Search
None
See application file for complete search history.

(56) References Cited

U.S. PATENT DOCUMENTS
2004/0076674 A1 * 4/2004 Ottersback et al. ........... 424/486

FOREIGN PATENT DOCUMENTS

| CN | 1468887 | * | 1/2004 |
|---|---|---|---|
| DE | 199 21 900 A1 | | 11/2000 |
| DE | 199 52 222 A1 | | 5/2001 |
| DE | 100 48 613 A1 | | 4/2002 |
| WO | WO 98/04296 A1 | | 2/1998 |
| WO | WO 02/085542 A1 | | 10/2002 |

OTHER PUBLICATIONS

Thome, J. et al., "Ultrathin Antibacterial Polyammonium Coatings on Polymer Surfaces," Surface and Coatings Technology, Elsevier, vol. 174-175, p. 584-587 (2003).

Kanazawa, Akihiko et al., "Polymeric Phosphonium Salts as a Novel Class of Cationic Biocides. III. Immobilization of Phosphonium Salts by Surface Photografting and Antibacterial Activity of the Surface-Treated Polymer Films," Journal of Polymer Science: Part A: Polymer Chemistry, vol. 31, p. 1467-1472 (1993).

Popa, Adriana et al., "Study of Quaternary 'Onium' Salts Grafted on Polymers: Antibacterial Activity of Quaternary Phosphonium Salts Grafted on 'Gel-type' Styrene-Divinylbenzene Copolymers," Reactive & Functional Polymers, vol. 1 (2002).

Lee, Sang Beom et al., "Permanent, Nonleaching Antibacterial Surfaces. 1. Synthesis by Atom Transfer Radical Polymerization," Biomacromolecules 2004, vol. 5, p. 877-882 (Feb. 2004).

* cited by examiner

*Primary Examiner* — David J Blanchard
*Assistant Examiner* — Tigabu Kassa
(74) *Attorney, Agent, or Firm* — Oliff & Berridge, PLC

(57) ABSTRACT

The present invention relates to a method for treating at least a surface of a substrate containing labile hydrogen atoms to confer to it cytotoxic properties or cell-adhesion properties, characterized in that it comprises at least a step consisting of exposing, within a liquid medium, said substrate or a surface thereof with at least a copolymer, said copolymer containing at least a monomer unit of type A including at least a reactive site able to attach to said substrate or said surface by covalent bonds and at least a monomer unit of type B including at least one molecule able to confer antimicrobial, antiviricidal and/or antifungicidal or cell-adhesion properties to said substrate or said surface, said step being carried out in efficient conditions to promote the covalent grafting of said copolymer to said substrate or a surface thereof.

20 Claims, 1 Drawing Sheet

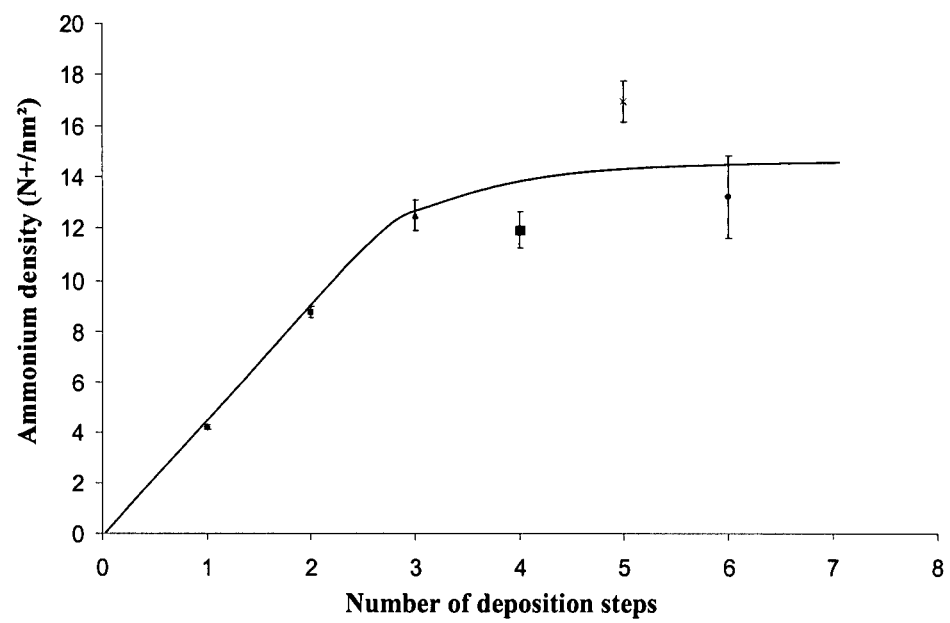

METHOD FOR TREATING SURFACES WITH COPOLYMERS

The present invention relates to a method for treating at least a surface of a substrate and more particularly to confer to it cell-adhesion properties or cytotoxic properties such as antibiotic, bactericidal, viricidal and/or fungicidal properties. It also concerns a statistical copolymer useful to perform this treatment and its preparation process.

For obvious reasons relating to healthy living, there is a need for materials capable of killing harmful micro organisms. Such materials could be used to coat surfaces of objects for providing them with permanent antibiotics, bactericidal, viricidal and/or fungicidal properties, to render them antiseptic and thus unable to transmit bacterial or fungicidal infections.

It is well known that charged molecules in solution are able to kill bacteria. However, it has been realized more recently that charges attached to surfaces can kill bacteria upon contact. All bear cationic, positive, charges like quaternary ammonium (Thome et al., Surface and Coating technology 174-175, 584-587, 2003), or phosphonium (Kanazawa et al., J. Polymer Sci. Part A: Polym. Chem. 32, 1467-1472, 1993; Popa et al., Reactive and Functional Polymers 55, 151-158, 2003). For example WO 98/04296 provides surfaces of substrates with permanent antibiotic, bactericidal, fungicidal or viricidal properties by attaching to them antibiotic molecules by covalent bonds via one or more "spacers". Said "spacer" comprises a head which can be grafted to the substrate, an alkyl chain and an outer terminal function which grafts the bio-active molecule. Said process is however not easy to implement in particular as far as two steps are required, the first one for grafting the spacer to the substrate and the second one for grafting the bio-active molecule to the terminal function of said spacer.

It is also well established that the grafting of high molecular weight polymers bearing cationic groups can be useful for conferring cytotoxic properties to solid surfaces.

Such treatments, which have not yet been industrialized, are promising because they could provide a new approach for the control of bacteria proliferation. Contrary to classical cytotoxic molecules, the treatment is permanent, the surfaces are reusable and no molecules are released in the environment. They also represent an interesting alternative against bacteria strains that have become resistant to antibiotics. In most cases the polymer is made from vinyl monomers containing primary, secondary or tertiary amino groups that are later converted to quaternary ammonium groups.

Two different approaches have been developed so far:

In the first case, preformed polymers are chemically grafted on the surface. For example WO 02/085542 describes a method to covalently attach to a surface, for example a glass plate, a N-alkylated polyvinylpyridine in order to render the surface bactericidal. However, the described method comprises at least three preparation steps to form the immobilized layer on the surface and huge amounts of reactive molecules with respect to the grafted ones.

In the second case, the polymer chain is grown directly from the surface using atom transfer radical polymerization. The attached neutral polymer is then converted to a polyelectrolyte by an in situ alkylation reaction. This method is for example described in Lee et al., "Permanent, non leaching, antibacterial surfaces", Biomacromolecules 5, 877-882, 2004.

However these methods present drawbacks that are major roadblocks against the industrialization of the process. They indeed require elaborate chemistry involving several steps in volatile organic solvents such as nitromethane.

It is moreover known from DE 199 52 222 copolymers of acryloylaminoalkyl which denote antimicrobial properties.

Therefore, there still exists a need to find new, simpler, more efficient methods for treating surfaces and conferring to them antimicrobial, antiviricidal and/or antifungicidal properties.

Moreover, there exists a need to find new methods to create appropriate cell-adhesion properties for a given substrate in order to extract micro organisms from a medium without killing them, for analytical purposes.

According to one aspect of the present invention, a method for treating at least a surface of a substrate containing labile hydrogen is provided to confer to it cytotoxic properties or cell-adhesion properties, characterized in that it comprises at least a step consisting of exposing, within a liquid medium, said substrate or a surface thereof with at least a copolymer, said copolymer containing at least a monomer unit of type A including at least a reactive site able to attach to said substrate or said surface by covalent bonds, and at least a monomer unit of type B including at least one molecule able to confer antimicrobial, antiviricidal and/or antifungicidal or cell-adhesion properties to said substrate or said surface, said step being carried out in efficient conditions to promote the covalent grafting of said copolymer to said substrate or a surface thereof.

According to an additional embodiment of the method of the invention, said method involves a consecutive step of drying after the step consisting of treating within a liquid medium, said substrate or surface thereof with at least a statistical copolymer.

According to another aspect of the invention, a cytotoxic or cell-adhesion statistical copolymer containing at least a monomer unit of type A and at least a monomer unit of type B is provided, characterized in that the monomer unit of type A contains at least a reactive site able to attach to a substrate or a surface containing labile hydrogen atoms by covalent bonds, and in that the monomer unit of type B contains at least one molecule able to confer antimicrobial, antiviricidal and/or antifungicidal properties or cell-adhesion properties to said substrate or said surface.

According to another aspect of the invention, the present invention concerns a preparation process of the cytotoxic or cell-adhesion statistical copolymer according to the invention, characterized in that a polymer comprising at least two reactive sites is reacted at least with:

a reagent that by reacting with at least one reactive site gives rise to a copolymer containing at least one reactive site able to attach to a substrate or a surface containing labile hydrogen atoms by covalent bonds and/or, another reagent that by reacting with at least one reactive site gives rise to a copolymer able to confer antimicrobial, antiviricidal and/or antifungicidal properties or cell-adhesion properties to a substrate or a surface thereof.

According to a further aspect of the invention, a composition comprising an efficient amount of a cytotoxic or cell-adhesion statistical copolymer according to the present invention is also embodied.

Finally, the present invention further relates to a substrate that, at least on its surface, has been provided with antibiotic, bactericidal, viricidal and/or fungicidal properties or cell-adhesion properties obtainable by a method according to the present invention and its uses.

Unexpectedly, the inventors have found that a statistical copolymer according to the invention allows a simple impregnation procedure for the treatment of the substrate. Moreover it is adapted to be solubilized in a ready-to-use solution.

The statistical copolymer according to the invention can be deposited on a large variety of substrates: glass, metals and metal oxides, plastics, wood, paper, leather, textiles such as cotton, jute, linen, hemp, wool, animals hair and silk, synthetic fabrics such as nylon, etc. More particularly, it is an object of the invention to provide a method to confer antimicrobial properties to solid surfaces possessing labile hydrogen atoms like thiols, amines or hydroxyl groups, and preferably hydroxyl groups.

Some of the substrates that may be treated according to the method of the present invention do not naturally contain such labile hydrogen atoms. In that case, the labile hydrogen atoms have to be generated in situ, by using standard activation methods such as disclosed hereafter.

According to a preferred embodiment of the present invention, the method of treatment is mainly dedicated to confer antibacterial properties to the substrate or the surface thereof. In other words, said method prevents the formation of biofilms and the development of bacterial colonies.

In particular, when the method is dedicated to confer bactericidal properties, it can find applications in medical (clinical hospital and personal care), as well as in domestic and industrial (food industry for example) environments. The shape of the surface can also vary according to the desired use.

The term "monomer" as used herein refers to a molecule or compound that usually contains carbon as its major component, is of relatively low molecular weight, and has a simple structure that is capable of assembling in polymeric chains by combination with itself or other similar molecules or compounds.

The term "monomer unit" as used herein refers to a constitutional unit of a polymer, which is formed starting from a unique monomer.

The term "copolymer" as used herein is defined as a polymer that is made up of more than one type of monomer.

The expression "statistical copolymer" or "random copolymer" as used herein interchangeably is defined as a copolymer that is made up of more that one monomer, and in which the different monomer units are randomly distributed in the polymeric chain. Unless stated otherwise, the term "copolymer" refers to statistical copolymer.

The expression "linear copolymer" as used herein is defined as a copolymer that is not branched.

The expression "block copolymer" as used herein is defined as a copolymer in which monomers of one type are adjacent to each other and form homopolymer segments, and the different homopolymer segments are linked together.

The term "labile hydrogen" as used herein refers to hydrogen atoms showing an increased reactivity due to their link with electrodonor atoms like oxygen, nitrogen and sulfur atoms.

The term "efficient conditions to" means the usual conditions to perform a chemical reaction defined by the usual parameters, i.e. pH, temperature, solvent, duration, etc., which fall within the standard skills of a man of the art.

For simplification reasons, in the framework of the invention, the term "cytotoxic", which is employed to qualify the modified properties of the substrate should be deemed to include not only the bactericidal or antibiotic properties, but also viricidal, fungicidal or in general any bioactive substance that is cytotoxic to any living cell the elimination of which is desired.

Statistical Copolymer

The statistical copolymer according to the present invention contains at least a monomer unit of type A including at least one reactive site able to attach to said substrate or said surface by covalent bonds and at least a monomer unit of type B including at least one molecule able to confer cytotoxic properties or cell-adhesion properties to said substrate or said surface.

The ratio between the two types A and B of monomer units contained in the statistical copolymer may be continuously adjusted to optimize the desired properties of the substrate or the surface of said substrate.

Typically, there is a monomer unit of type A that gives to the statistical copolymer the ability to anchor to the substrate or the surface of said substrate. Preferably said monomer unit of the type A contains a silane group, such as an $(C_1-C_4)$ alkoxysilane, for example a methoxysilane and a ethoxysilane.

The monomer units of type A are available commercially or by simple derivatization of existing monomer units.

The monomer unit of type B is selected for its ability to confer the desired cytotoxic properties or cell-adhesion properties as described above, to the substrate or the surface of said substrate. Among the monomers of type B that may be part of the statistical copolymer the following ones may be cited:

Monomers imparting antibiotic, bactericidal, viricidal properties, which may contain aminopenicillanic acid that is known to interact with cell membranes, Monomers imparting bactericidal properties, which may contain positively charged groups such as quaternary ammonium groups, quaternary phosphonium groupsand guanidinium groups, Monomers imparting viricidal properties, which may contain quaternary ammonium groups (especially for bacterial viruses), and Monomers imparting fungicidal properties, which may contain quaternary ammonium groups, quaternary phosphonium groups and guanidinium groups.

Where the monomer unit of type B is selected for conferring to said copolymer some ability to extract micro-organisms from a medium without killing them, only the previously cited monomers having not too high toxicity are convenient.

Thus, monomers containing quaternary ammonium groups having at least one, preferably two and more preferably three short alkyl chain(s) for example in $C_1$ to $C_6$, and in particular in $C_1$ are particularly advantageous for achieving the expected cell-adhesion.

Trimethylammonium groups are more particularly preferred.

In any case, the amount of monomer unit of the type B within the copolymer is advantageously sufficient to impart the required effect to the substrate or the surface thereof, when the copolymer is present in the composition ready for the impregnation at a concentration of 1 mg/mL or more.

The selection of each monomer of the statistical copolymer can vary according to the required effect of the copolymer in view of the desired properties for the substrate or the surface thereof.

Each monomer unit may be distributed along the copolymer chain in no specific order and the percentage of monomer unit of type A out of the total amount of monomer units may vary between 1% to 20%, preferably between 5% to 10% whereas the percentage of monomer of type B out of the total amount of monomer units may vary between 80% to 99%, preferably between 90% to 95%.

The statistical copolymer may contain various monomer units of type A with different types of reactive sites able to attach to the substrate or the surface of said substrate, by covalent bonds.

The statistical copolymer may also contain various monomer units of type B with different bioactive specificities. For example, this enables to obtain treated substrates endowed with various antibiotic properties and to obtain a particular antibiotic spectrum for a given substrate.

The statistical copolymer is preferably a linear copolymer. But according to another aspect of the invention, the statistical copolymer may be cross-linked after the impregnation procedure, to improve the stability and the durability of the grafted layer. It is however obvious that the number of cross-linking points must not exceed a number that could affect the required effect or the grafting affinity.

The statistical copolymer may comprise a polymeric chain backbone chosen among polyethylene, polyacrylamide, polystyrene, optionally substituted on the phenyl group by a $(C_1-C_4)$alkyl, polyvinylalcohol, polyallylamine, polyallylalcohol, polyvinylbenzyl, polyamine such as polyethyleneimine, polymethacrylate such as polymethylmethacrylate, polyether, poly(ethylene-alt-succinimide) and poly(diallyldimethylammonium) which inherently contains a quaternary ammonium group and may be represented by the following formula:

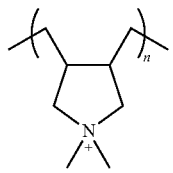

Some of said various polymeric chain backbones are illustrated hereinafter in schemes 1 to 6.

According to one embodiment of the instant invention, the reactive sites of monomer unit of type A and/or the molecules conferring cytotoxic properties or cell-adhesion properties of monomer unit of type B may, independently one from each other, be linked to concerned monomers via a lateral chain.

The lateral chain on the one hand forming the lateral chain of the monomer unit of type B and on the other hand forming the lateral chain of the monomer of type A may be of various structures.

The lateral chain of the monomer unit of the type B can be represented by the following formula

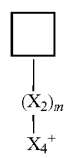

wherein
☐ means the link to monomer B
m is 0 or 1,
$X_2$ represents an amine, an amide, an ester or a ketone function, an oligoethylene glycol, an arylene group, a $(C_1-C_6)$alkylarylene, or a $(C_1-C_8)$alkylene which may be interrupted by anyone of an amine, an amide or a ketone function, and $X_4^+$ represents:
a trialkylammonium of formula

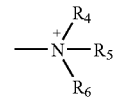

wherein $R_4$, $R_5$ and $R_6$ independently represent a $(C_1-C_{12})$alkyl, hydroxy$(C_1-C_{12})$alkyl or fluoro$(C_1-C_{12})$alkyl group,
a $(C_1-C_4)$alkylpyridinium group of formula:

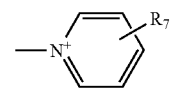

wherein $R_7$ represents a $(C_1-C_4)$alkyl,
a $(C_1-C_4)$alkylimidazolium group of formula:

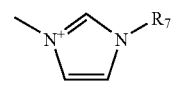

wherein $R_7$ is as described above,
a guanidinium group of formula.

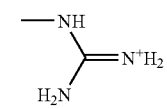

a trialkylphosphonium of formula

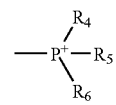

wherein $R_4$, $R_5$ and $R_6$ are such as defined above, or alternatively

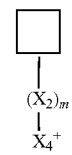

represents a monomer unit containing a 5- or 6-membered saturated ring containing a quaternary ammonium. An example of this alternative is represented with a statistical copolymer manufactured starting from the homopolymer poly(diallyldimethylammonium) of formula:

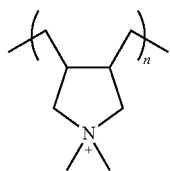

The lateral chain of the monomer unit of type A can be represented by the following formula

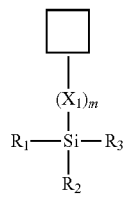

wherein
□ means the link to monomer A
m is 0 or 1,
$X_1$ represents an amine, an amide, an ester or a ketone function, an oligoethylene glycol, an arylene group, a ($C_1$-$C_6$)alkylarylene group, or a ($C_1$-$C_8$)alkylene group which may be interrupted by anyone of an amine, an amide or a ketone function, one of the carbon atom in the ($C_1$-$C_8$)alkylene being optionally replaced by a quaternary ammonium, a quaternary phosphonium, a ($C_1$-$C_4$)alkylpyridinium, a ($C_1$-$C_4$)alkylimidazolium or a guanidinium group,
at least one of $R_1$, $R_2$ and $R_3$ is able to react with an hydroxyl, a thiol or an amine group, preferably is a group showing a character of leaving groups, and the other one or two radicals chosen among $R_1$, $R_2$ and $R_3$ can independently represent a ($C_1$-$C_4$)alkoxy, or any one of the group $R_1$, $R_2$ and $R_3$ is a group showing character of leaving group,
or alternatively

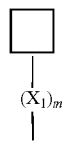

represents a part of monomer unit containing a 5- or 6-membered saturated ring containing a quarternary ammonium.

Groups able to react with an hydroxyl, a thiol or an amine group are more particularly described in the framework of the description of the preferred statistical copolymers.

The molecular weight of the copolymer may vary between $10^3$ and $10^6$ g/mol depending of the nature of the copolymer. More preferably it is of the order of $10^5$ g/mol.

According to a preferred aspect of the invention, any of the monomer of type A or of type B may contain chemical groups that improve the solubility within the liquid medium. In particular, according to a most preferred embodiment detailed hereafter, it may be advantageous to use water-soluble copolymers for user-friendliness reasons. In this particular case, any or both of the monomer of the A or the B type can include hydrophilic groups.

The statistical copolymers according to the present invention are synthesized by copolymerization of monomers using methodologies well known to those skilled in the art.

The present invention relates more particularly to a statistical copolymer containing both a bactericidal and/or fungicidal substance, which is preferably a positively charged groups and silane groups, intended to covalently attach to the surface by generating siloxane bonds.

The positively charged groups are advantageously quaternary ammonium groups, quaternary phosphonium groups and/or guanidinium groups.

The silane group is preferably a trialkoxy or a trichlorosilane, which as such are well-known surface modifiers.

The copolymer is covalently attached to the surface through the coupling of the silane groups with the surface hydroxyls, whereas the quaternary ammonium groups provide the necessary positive charges for the cytotoxic or cell-adhesion activity.

In other words, in a preferred embodiment, monomer unit of type A comprises a silane group, and monomer unit of type B comprises a quaternary ammonium group.

A monomer unit of type A can be represented within the copolymer by the compound of formula (I)

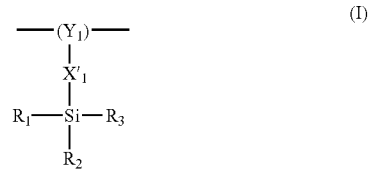

wherein
at least one of $R_1$, $R_2$ and $R_3$ is able to react with an hydroxyl, a thiol or an amine group, preferably is a group showing a character of leaving group.

$X'_1$ represents an arylene group, a ($C_1$-$C_6$)alkylenarylene group, or a ($C_1$-$C_8$)alkylene group, optionally one of the carbon atom in the alkylene group being replaced by a nitrogen atom, preferably being a quaternary ammonium, by a a quaternary phosphonium, by a ($C_1$-$C_4$)alkylpyridinium, by a ($C_1$-$C_4$)alkylimidazolium, or by a guanidinium group, $Y_1$ is a part of the polymeric chain backbone and can advantageously be an ethylene optionally substituted by a methyl group, an acrylamide, an ethyleneimine, a methylmethacrylate group or a propylene glycol.

The "at least one" of $R_1$, $R_2$ and $R_3$, i.e. the group showing a character of leaving group, may for example represent an halogen atom, preferably a chlorine atom; an hydroxyl group; a halogeno($C_1$-$C_{10}$)alkyl, preferably a halogeno($C_1$-$C_6$) alkyl, and most preferably a halogeno($C_1$-$C_4$)alkyl; or a ($C_1$-$C_{10}$)alkoxy group, preferably a ($C_1$-$C_6$)alkoxy group, and most preferably a ($C_1$-$C_4$)alkoxy group.

The other one or two radicals chosen among $R_1$, $R_2$ and $R_3$ can independently represent a ($C_1$-$C_4$)alkyl, or any one of the groups showing a character of leaving group as described above.

More particularly, $R_1$, $R_2$ and $R_3$ are identical, which constitutes a preferred embodiment of the invention.

A monomer unit of type B can be represented within the copolymer by the compound of formula (II)

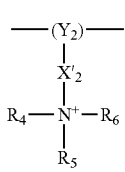

(II)

wherein $R_4$, $R_5$ and $R_6$ independently represent a $(C_1-C_6)$alkyl, a hydroxyl$(C_1-C_6)$alkyl or a fluoro$(C_1-C_6)$alkyl, $X'_2$ represents a $(C_1-C_4)$alkylene, an oligoethylene glycol or an arylene group, $Y_2$ is a part of the polymeric chain backbone and can advantageously be an ethylene optionally substituted by a methyl group, an acrylamide, an ethyleneimine, a methylmethacrylate or a propylene glycol.

When the monomer comprises a quaternary ammonium, the counterion $X_3^-$ may be a halogen, a mesylate, a tosylate, a sulfonate, a phosphate, a hydrogenophosphate, an ammonium dihydrogenophosphate, a sulfate or a nitrate.

The term "$(C_1-C_6)$alkyl" as used herein refers to a straight or branched-chain hydrocarbon radical of one to six carbon atoms and their cyclic derivatives, unless otherwise indicated. Included within the scope of this term are such moieties as methyl, ethyl, isopropyl, n-butyl, t-butyl, t-butylmethyl, cyclopropyl, n-propyl, pentyl, cyclopentyl, n-hexyl, cyclohexyl, cyclohexylmethyl, 2-ethylbutyl, etc.

The term "halogen" refers to a fluorine, chlorine, bromine or iodine atom. Bromine and chlorine are preferred halogen atoms in the framework of the present invention.

The term "alkoxy" refers to alkoxy radical made up of an oxygen radical bearing a saturated straight or branched chain hydrocarbon radical. Included within the scope of this term are methoxy, ethoxy, propoxy, n-butoxy, isobutoxy, sec-butoxy, t-butoxy, n-pentoxy, isopentoxy, sec-pentoxy, t-pentoxy . . . and the like.

The term "arylene" as used herein refers to a bivalent radical group selected among phenylene, biphenylene, naphtylene, dihydronaphtylene, tetrahydronaphtylene, indenylene and indanylene.

The monomer unit of type B have a hydrophilic character because of their positively charged group. Controlling the proportion of the monomer unit of types B and A allows creating a polymer that is water-soluble on the one hand, and possesses a strong binding affinity to substrates with surface hydroxyl groups on the other hand.

Therefore, according to a most preferred embodiment, the statistical copolymer is water-soluble. The percentage of monomer unit of type A and monomer unit of type B based on the average total number of monomers of the copolymer is then adjusted to ensure the solubility of the statistical copolymer in aqueous solutions.

According to this aspect of the invention, the percentage of monomer unit of type A out of the total amount of monomer units may vary between 1% to 50%, preferably between 5% to 15% whereas the percentage of monomer of type B out of the total amount of monomer units may vary between 50% to 99%, preferably between 85% to 95%.

In the framework of this particular embodiment, the water-soluble statistical copolymer can have a molecular weight of at least $10^4$ g/mol, more preferably $5.10^4$ g/mol, and most preferably $10^5$ g/mol.

The density of active cytotoxic or cell-adhesion sites on the obtained treated substrate may be adjusted by varying the ratio between the number of monomers of type A and B.

Said statistical copolymer can be prepared according to known synthesis techniques. In accordance with an example of feature of the invention, the water-soluble statistical copolymer wherein $Y_1$ and $Y_2$ are ethylene groups, $X_1$ is a N,N,N,N-dimethylphenylene-propylene-ammonium, $R_1$, $R_2$, $R_3$ are methoxy groups, $R_4$ and $R_6$ are methyl groups, $R_5$ is a butyl group and $X_2$ is a phenylene group, may in particular be prepared according to scheme 1 below. The symbols x and y in the FIGURE are the relative proportions of the possible monomer units which the statistical copolymer may comprise.

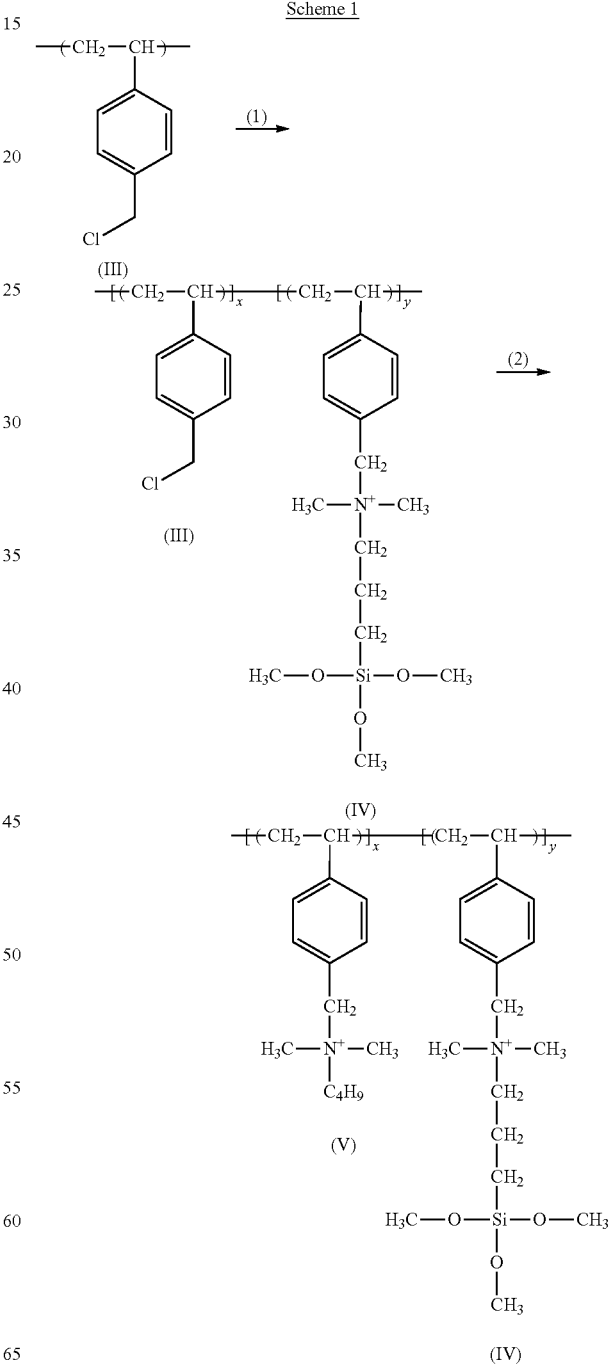

Scheme 1

A polymer comprising monomers of poly-(vinylbenzyl-chloride) (indicated as (III) in Scheme 1) is reacted in a first step (step 1) with an dimethylaminoalkyltrimethoxysilane, for example $(CH_3)_2N(CH_2)_3Si(OCH_3)_3$, for example in tetrahydrofuran at reflux temperature during for example 24 hours, for example in a molar ratio comprised between 1 and 30%, more preferably between 5 and 10%. The polymer formed contains a fraction, y, of modified monomers of formula (IV) and a fraction, x=1−y, of unmodified monomers of formula (III). Since the reaction is not necessarily quantitative, y has to be determined independently. Said obtained polymer can be then reacted in a second step (step 2) with a tertiary amine such as $(CH_3)_2N(CH_2)_3CH_3$ for example in a molar ratio between 1 and 10, more preferably between 1.5 and 2, for example in excess, for example in tetrahydrofuran at reflux temperature during for example 6 hours. Monomers of formula (III) are transformed in monomers of formula (V) whereas monomers of formula (IV) are unaffected by the reaction. The final polymer is a statistical polymer consisting of monomer units of formula (IV) and (V). When the tertiary amine is in large excess, the final polymer essentially comprises a fraction, x, of monomers of formula (V) and a fraction, y, of monomers of formula (IV). Typically it may comprise 90 to 95% of monomer units of formula (V) and 5 to 10% of monomers of formula (IV), based on the total number of monomers of the copolymer. Monomer units of formula (IV) and (V) are the monomers of type A and B previously described. The former ones confer the binding properties to the substrate, whereas the latter ones confer the cytotoxic properties to the grafted polymer film.

During the course of the reaction, precipitation of the materials can occur. To avoid precipitation ethanol (or methanol) can be added up to complete solubilization of the material. After refluxing for 12 hours, the mixture can be either i) cooled, filtrated and washed with ether or ii) evaporated and dried.

The synthesis of one of said statistical copolymers has been illustrated thereafter in the examples.

Further examples of preparation process are given below in scheme 2 to scheme 6 starting from other polymers.

Scheme 2

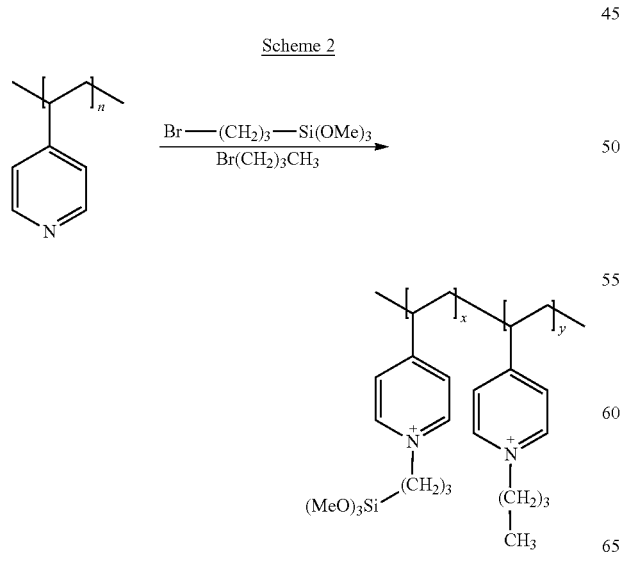

Scheme 3

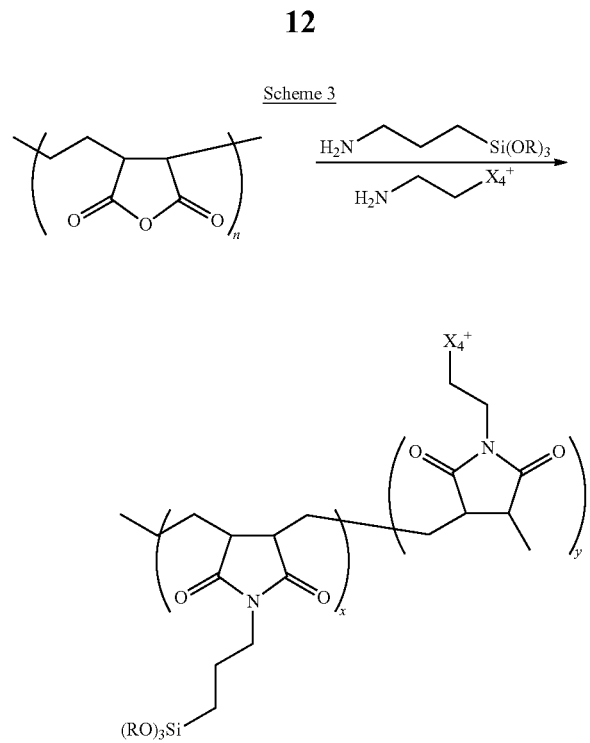

Scheme 4

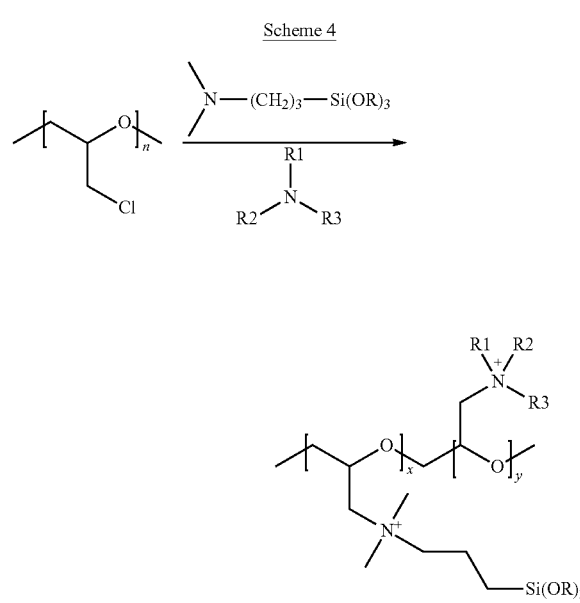

Scheme 5

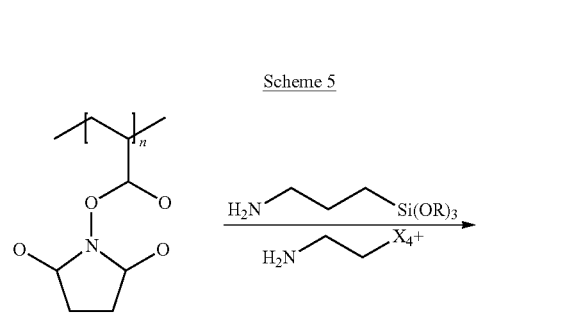

-continued

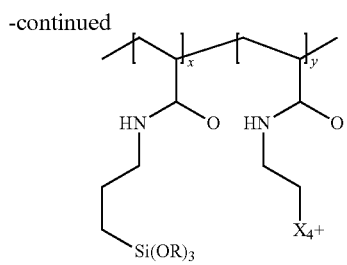

Scheme 6

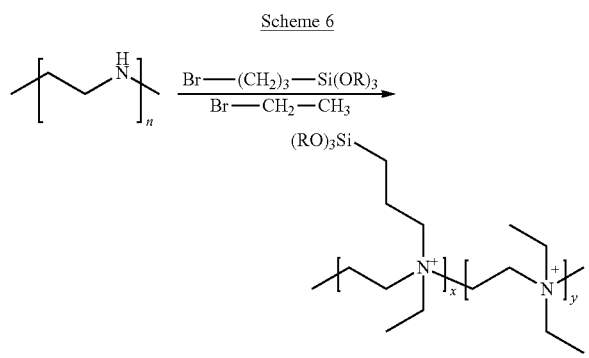

In the preceding schemes, $X_4^+$ is such as defined above; $R_1$, $R_2$ and $R_3$ independently represent a $(C_1\text{-}C_6)$alkyl, a hydroxyl $(C_1\text{-}C_6)$alkyl or a fluoro$(C_1\text{-}C_6)$alkyl when linked to a nitrogen atom and R is a $(C_1\text{-}C_4)$alkyl when linked to the silicium atom to give a —Si(OR)$_3$ group.

Therefore, the present invention further relates to a preparation process of the cytotoxic or cell-adhesion statistical copolymer according to the invention, characterized in that a starting polymer comprising at least two reactive sites is reacted at least with:
- a reagent that by reacting with at least one reactive site gives rise to a copolymer containing a reactive site able to attach to a substrate or a surface containing labile hydrogen atoms by covalent bonds and/or
- with another reagent that by reacting with at least one reactive site gives rise to a copolymer able to confer antimicrobial, antiviricidal and/or antifungicidal properties or cell-adhesion properties to a substrate or a surface thereof Both reactions may be performed in same time or successively, i.e. in two steps in an indifferent order.

The reactive sites which may be present on the starting polymer, which are illustrated in the here above schemes 1 to 6, may be chosen among halogen atoms, activated carboxylic acids such as anhydrides, acyl halides for example acyl chlorides, activated esters, for example N-hydroxysuccinimid esters and amines, for example aliphatic or aromatic amines.

These polymers are well known to the one skilled in the art or are commercially available.

According to a preferred embodiment of the present invention, the starting polymer is a homopolymer.

According to another preferred embodiment of the present invention, the preparation process according to the present invention is performed in two steps, the first one, giving rise to only one type of monomer units, i.e. of type A or type B and leaving a portion of the starting monomer units unreacted and the second one giving rise to monomer units of the other type from the unreacted monomer units after the first step, whereas the monomer units transformed in the previous step stay unchanged during this second step.

Alternatively, the statistical copolymer according to the present invention may be manufactured via polymerization starting from two distinct monomers. Said alternative is illustrated in Example 3.

The use of said particular statistical copolymer comprising monomer units of formula (I) and monomer units of formula (II) according to the present invention presents numerous advantages. Indeed the deposition method is extremely simple: the modification of the surface with this particular statistical copolymer involves a one-step reaction in water, followed by a drying step. Water can indeed be the liquid medium, provided the statistical copolymer comprises a sufficient amount of quaternary ammonium groups, which renders said copolymer soluble in water. This characteristic is a further advantage of the present invention over the known methods to treat surfaces, which are generally performed in organic solvents that can degrade the substrates to be treated and are not environmentally friendly.

Composition Comprising a statistical copolymer

The present invention also relates to a composition comprising an efficient amount of statistical copolymer.

The solvent optionally present in the composition may be any one that can solubilize the copolymer. In the preferred embodiment of water-soluble copolymer, the composition is miscible with water and most preferably contains in majority water as a solvent. Other solvents such as dimethylsulfoxide, dimethylformamide, acetonitrile, methanol, and ethanol can also be used.

The concentration of the statistical copolymers in said composition is any amount that provides the desired cytotoxic or cell-adhesion properties to the substrate or the surface of said substrate after the treatment. This concentration will vary with respect to the molecular structure, the desired properties, and the solvent. Typically, the weight concentration of the statistical copolymer in the composition can vary between 5 and 10% in the case of water, and between 10 and 50% in the case of ethanol.

Method of Treatment

The present invention relates to a method for treating a surface of a substrate containing labile hydrogen atoms to confer to it cytotoxic or cell-adhesion properties, characterized in that it comprises at least a step consisting of exposing, within a liquid medium, said substrate or said surface thereof with at least a copolymer, said copolymer containing at least a monomer unit of type A including a reactive site able to attach to said substrate or said surface by covalent bonds and at least a monomer unit of type B including at least one molecule able to confer expected properties of said substrate or said surface, said step being carried out in efficient conditions to promote the covalent graft of said copolymer to said substrate or said surface thereof.

For the purpose of performing the method of treating a surface according to the present invention block copolymer may also be used, with the proviso that they comply with the hereabove described characteristics in terms of presence of the required monomer units.

In other words, all the description of each of the monomer unit of type A and of type B in the preceding paragraph "STATISTICAL COPOLYMER" apply to any copolymer used for the method of treatment according to the present invention.

The method using the statistical copolymer more particularly described above, comprising a silane group in monomer A and a quaternary ammonium group in monomer B, to impregnate a surface of a substrate to confer bactericidal and/or fungicidal properties also forms part of the invention.

The liquid medium is advantageously an aqueous medium.

The method according to the present invention may comprise, previous to the treatment step, a step consisting in chemically activating the substrate surface to generate labile hydrogen atoms. For instance, a plasma treatment in a gas such as oxygen or in air can generate hydroxyl groups at the surface of polyethylene or polypropylene films.

According to a preferred embodiment, the invention relates to a method for treating a surface of a substrate containing labile hydrogen atom as set forth in the above, and further comprising a drying step.

The drying step, which can also be referred to as a "curing step", creates dehydration conditions that facilitate cross-linking of the silanol groups with the surface hydroxyl groups, and also between themselves.

The drying step can be performed at a temperature ranging from 60 to 150° C., preferably from 80 to 110° C. and most preferably from 100 to 110° C.

Said drying step may advantageously been carried out during a period ranging from 10 to 100 min, for example between 50 and 90 minutes.

The drying temperature may indeed influence the film stability and particularly the stability during contact with water. The films dried at the highest temperature, i.e. above 90° C. and for example at 110° C., are perfectly stable. This was checked by monitoring the number of quaternary ammonium groups present in the films as a function of time. There is no evolution of the charge density even after 5 hours of immersion in water. For samples dried at the lowest temperature, i.e. under 80° C. and for example at 70° C., the charge density drops to half of its original value after about 20 minutes of immersion. This indicates that some of the polymer chains can be detached from the substrate, either because they were simply physisorbed rather than chemically grafted, or because they get hydrolyzed in smaller fragments that are more water-soluble. After this initial decrease, the number of quaternary ammonium no longer changes and the remaining part of the film is stable over long period of times.

The rationale for high temperature curing is that it creates low humidity conditions that facilitate the cross-linking reaction between the surface hydroxyl groups and the silanol groups of the polymer chains. It also favors internal cross-linking between the silanol groups of the polymer chains. Altogether, these two effects lead to a well-anchored and water-insoluble gel structure.

Substrate

The present invention further relates to a substrate provided with antibiotic, bactericidal, viricidal or fungicidal properties obtainable by a method according to the present invention. More generally it relates to substrates to which a particular cytotoxic surface or cell-adhesion surface property can be conferred by a proper chemical treatment.

Said treated substrates do not request particular storage conditions to keep their modified properties. The surface treatment is indeed advantageously resistant to water and other solvents up to certain limits.

In the framework of the preferred embodiment as exposed above, a substrate endowed with bactericidal and/or fungicidal propertied is obtained. In this case, the density of active antibiotic sites per unit surface area may range from $10^{14}$ to $10^{16}$ per $cm^2$.

When the substrate may be used to promote cell-adhesion without bactericidal activities, the density of active sites has to be adjusted with respect to the chemical nature of the considered reactive site and more particularly by taking account its cytotoxic power. This adjustment may be performed by the man skilled in the art.

For example, when the cell-adhesion is promoted by a substrat exhibiting trimethylammonium groups as reactive sites, the density in active sites per unit surface is generally equal or lower than $10^{14}$ per $cm^2$.

The substrate is then to be considered as a kind of probe useful to perform analysis of the isolated bacteria. This tool is for example of interest in the food industry where it is always avoided to stop the production line.

The conditions of deposition of the statistical copolymer more particularly described above, comprising a silane group in monomer unit of type A and a quaternary ammonium group in monomer unit of type B, on cotton, glass and silicon oxide is illustrated thereafter in the examples and the corresponding antimicrobial activity of such surfaces has then been tested against $E.$ $coli$.

Depending on the mass of said copolymer deposited, the thickness of the deposited layer can range between 1 and a few tens of nanometers for the copolymer as illustrated in the examples. The thickness can advantageously be measured by ellipsometry on silicon wafers. The resulting layer is a thin polymeric gel that is very robust against solvents and mechanical friction.

The charge density (for example, as measured by fluorescein derivatization) for good cytotoxic properties against $E.$ $coli$ for the copolymer as illustrated in the example is advantageously over $10^{15}$ per $cm^2$, more preferably over $10^{16}$ per $cm^2$ and can typically range between $10^{14}$ and $10^{16}$ per $cm^2$.

The invention more particularly relates to a substrate endowed with antibiotic properties characterized in that monomer of type B contains quaternary ammonium and the density of active antibiotic sites per unit surface area ranges from $10^{14}$ to $10^{16}$ per $cm^2$.

The density of quaternary ammonium groups can for example be measured by the fluorescein complexation method.

It has been demonstrated and illustrated in the examples that substrates treated with the illustrated copolymer can kill all absorbed $E.$ $coli$ bacteria within 10 minutes.

A treated substrate, in particular when the substrate is cotton or glass, may be retreated for further impregnation and drying steps according to the method as described above. Said retreated substrates are also encompassed within the scope of the present invention.

Use of Substrate

The present invention also encompasses the use of the substrate of the invention described above, and which can be obtained by the method described above and illustrated in the following examples.

The use of the surfaces of the invention for decontamination purposes may be of interest to a number of industrial fields, such as health, hygiene and agro-alimentary industries. Examples are:

- using a surface for the production of containers for medical use, such as bottles, pouches, or tubes, in particular disposables;
- using a surface for the production of medical apparatus for ex vivo or in vivo organ treatment, such as renal dialysis cartridges;
- using a surface for the production of materials or equipment for dentistry or for cleaning teeth;
- using a surface for the production of implantable devices such as osseous or vascular prostheses;
- using a surface for the decontamination of domestic fluids, in particular water and beverages (fruit juices, milk, wine, etc), or other fluid foodstuffs;

using a surface for the decontamination of industrial fluids, for example cutting fluids, lubricants or petroleum fluids such as gasoil, gasoline or kerosene.

The present invention further relates to the use of substrates of the present invention, as a tool to isolate bacteria from a media.

The following examples illustrate the present invention.

EXAMPLE 1

Synthesis of a Statistical Copolymer and Characterization

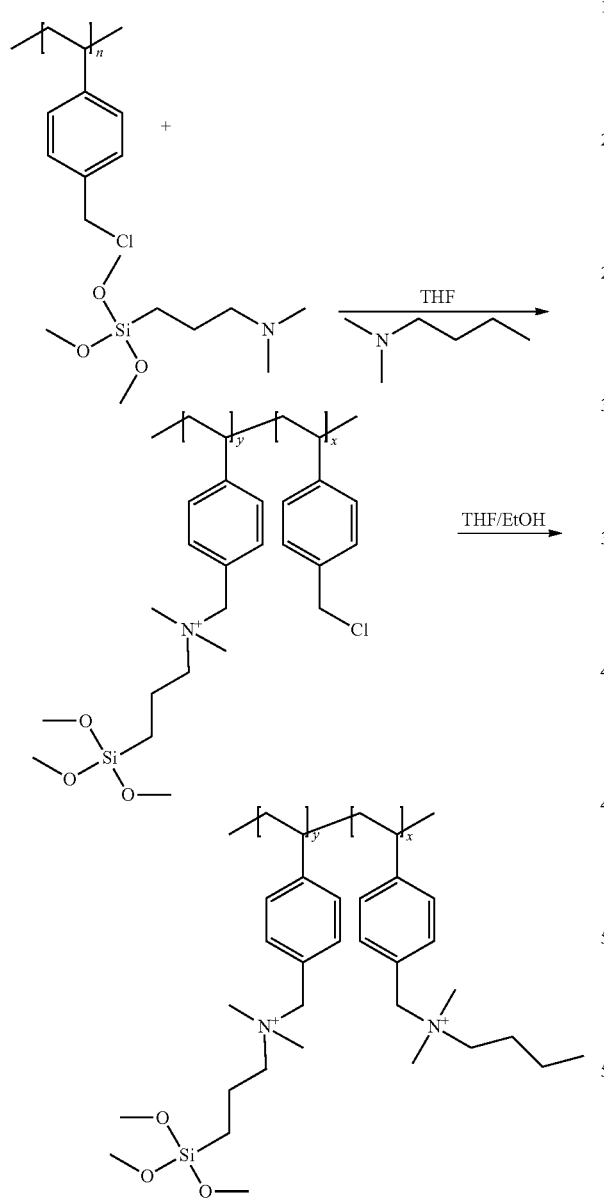

The starting material was poly-(vinylbenzylchloride) (PVBC for short) and was purchased from Sigma as a 60/40 mixture of meta and ortho isomers. It was dissolved in dry tetrahydrofuran (0.44 gram in 30 ml) by stirring at room temperature during 30 minutes. Dimethylaminopropyltrimethoxysilane $(CH_3)_2-N-(CH_2)_3-Si(OCH_3)_3$ (Sigma) was then added in a 1% to 10% stoichiometric ratio and the mixture was stirred under reflux during 4 hours until the nucleophilic addition between PVBC and dimethylaminopropyltrimethoxysilane was completed. After cooling, the remaining VBC monomers were reacted with a large excess (2 ml) of N,N dimethylbutylamine $(CH_3)_2N-(CH_2)_3-CH_3$). The mixture was heated at reflux overnight. Ethanol is added to the mixture to avoid precipitate formation. The reaction mixture is evaporated and dried in vacuo. The final product has the aspect of a white powder and is a fully quarternized poly-(vinylbenzyl) statistical copolymer (PVB-Si-Q for short) containing approximately 10% of trimethoxysilane and 90% of dimethylphenylene-propylene-ammonium side groups. This stoichiometry insures the solubility of the polymer in water up to a concentration of at least 1.5 mg/ml. The H1-NMR was consistent with the expected molecular structure for the functionalized statistical polymer (scheme 1). There was no evidence for the presence of the initial benzyl-chloride side groups (formula (III)). They have all been converted into either a silane side group or a quaternary ammonium side group. The results of the elemental analysis for a typical sample were also in good agreement with the expectations: 59, 4.7 and 1.5% for C, N and Si respectively. Using this data, one derives that 14% of the monomers have silane functionality and are thus able to bind covalently to the substrate.

Preparation of the Ready-to-Use Solution

Due to its cationic charges, the PVC-Si-Q polymer could be readily dissolved in Milli-Q water (pH 6) up to concentrations of 1.5 mg/ml. An ultrasonic bath was used to speed up the dissolution. The solution at room temperature was clear and showed no evidence of aggregates.

EXAMPLE 2

Deposition of the Polymer on the Solid Substrates

Scheme 7.
Deposition of the statistical quaternized copolymer on hydroxylated surfaces

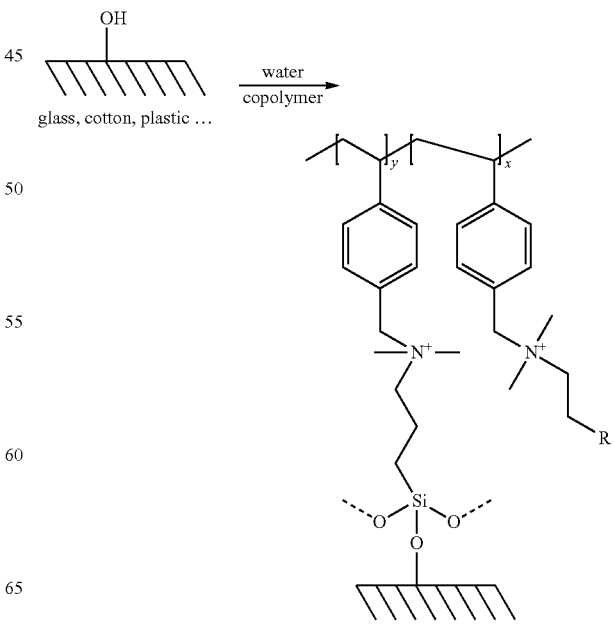

I. Material and Methods

Deposition of the Polymer on the Solid Substrate

In the case of cotton fabrics, 0.5×2 cm² pieces were cut with scissors and imbibed with droplets of the polymer solution at 1 mg/ml. At first, 240 µL was deposited, corresponding to a polymer mass of 240 µg on a total surface of 200 cm². The cotton was then put in an oven for drying during 30 minutes. Two different temperatures were tested, either 70 or 110° C. The procedure was repeated up to 6 times in order to produce a thicker and more homogenous deposit. Assuming the density of the layer is close to unity, the estimated thickness deposited at each step was 12 nm.

In the case of glass slides, single droplets of 100 µL were spread on the entire surface of 13.5 cm² and let sit for 15 to 30 minutes. The water layer was then evaporated in an oven at 110° C. Assuming the density of the layer is close to unity, the estimated thickness deposited was 8 and 80 nm for the selected polymer concentrations of 0.1 and 1 mg/ml, respectively.

Bacterial Strains and Media (LB and 63B1):

*Escherichia coli* (*E. coli*, Pasteur 16775) was chosen as an example of a Gram-negative bacteria. They were transferred from the frozen state onto Agar plates (diameter 90 mm, Columbia+5% sheep blood, Biorad S.A., France) and incubated overnight at 37° C. One colony was then transferred to a test tube containing 2 ml of liquid nutrient solution (LB) at 37° C. and allowed to divide during two hours. The final optical density at 590 nm was 0.5, corresponding to a bacteria concentration of the order of $10^4$ per ml. 100 µL of this solution was then diluted in a mixture of 5 ml of 63B 1 (nutrient broth) plus 100 µL of 20% glucose solution in water. After 3 hours in this growth medium at 37° C., the optical density at 590 nm returned to 0.5. The bacteria were thus in their exponential growth phase and could be used in the biocidal experiments.

Description of Substrates a) Cotton

Large fabrics of cotton were supplied by a commercial manufacturer (Tencel, Spondon, Derby, DE21 7BP, England). They were free of dyes or processing additives. We have checked by XPS that their carbon (75%) and oxygen (25%) content was in agreement with pure cellulose, with no traces of contaminants. The average fibre diameter was 10 µm and consequently the specific surface could be estimated at 0.4 m²/gram. Before use, the cotton fabric was cut in small pieces and these samples were repeatedly washed in distilled water and dried at 70° C. during 20 minutes.

b) Glass

Degreased planar glass sides (76×26 mm2) were purchased from Sigma. They were cleaned by the Piranha method (70/30 mixture of H2SO4—H2O2) at 60° C. during 30 minutes. The resulting surface was very hydrophilic, with a high proportion of accessible OH groups. The slides were then rinsed in distilled water and dried during 10 minutes at 70° C.

Oxidized silicon wafers, diameter 2.54 cm and thickness 500 µm, (Siltronix, France) were also used and cleaned by the same procedure. Their extremely flat and highly reflecting surface allows ellipsometry thickness measurements of the deposited organic layer.

II. Measurements

Ellipsometry Measurements

A rotating analyzer ellipsometer (Plasmos model SD 2300, New Jersey, USA) operating at 632.8 nm and at 70° incidence angle was used to measure the PVB-Si-Q polymer layer thickness on the silicon wafer substrates. Data were taken at twenty-five different spots on each sample with a beam spot of 1 mm.

X-Ray Photoelectron Spectroscopy

The XPS analysis was performed with a SSI model SSX-100 spectrometer from VG-scientific using a focused monochromatic $AK_q$ radiian (1486.6 eV). The angle of incidence of the collimated X-ray beam was 35° and the take-off angle for the electrons was 35° with respect to the surface. The spot had an elliptic shape, with minor and major axes of 250 and 750 µm respectively for survey spectra (X-ray power 200 W) and of 300 and 350 µm for detail spectra (X-ray power 60 W). To avoid charging effects in the case of non-conducting cotton samples, a flood gun was used (energy of the soft electrons fixed at 20 eV). The decrease of the Fermi level was accounted for and the binding energies were corrected by using the $Au_{4f}^{7/2}$ peak energy at 84.0 eV as a calibration. The $C_{1s}$ carbon peak position for the C—C and C—H components was at 284.8 eV. The spectrometer was operated in the constant analyzer energy (CAE) mode at a pass energy of 150 eV for survey spectra and 50 eV for detail spectra. The transparency of the spectrometer for the electrons ensures a high signal-to-noise ratio. The instrument resolution was estimated from the full width at half maximum (FWHM) of the $Au_{4f}^{7/2}$ peak. For a spot size of 300×300 µm², it was 0.9 eV at resolution 2 (i.e. pass energy 50 eV) and 1.5 eV at resolution 4 (pass energy 150 eV). The linearity of the spectrometer was checked by using the $CU_{3s}$ at 122.4 eV and $Cu_{2p}^{3/2}$ at 932.4 eV.

All peaks were resolved by using the spectra processing program included in the XPS operating system by the manufacturer. The adjustable parameters for the best-fit search were the position of the peak maxima, the FWHM and the peak amplitude. A non-linear background was subtracted and the peak shape was assumed to be 100% Gaussian. A mixture of Lorentzian and Gaussian shapes yielded no improvement in the fitting. The peak positions were determined with an accuracy of ±0.2 eV. The peak widths were 1 eV for $Si_{2p}^{3/2}$, 1.3 eV for $C_{1s}$, 1.6 eV for $N_{1s}$.

The quantitative analysis of the surface composition was estimated from the integrated peak areas normalized by the relative sensitivity Scofield factors (Scofield, J. H., J. Electron Spectroscopy 8, 129, 1976), the electron mean free path and the apparatus transmission function. The relative sensitivity factors depending on the nature of the element were 0.87, 1.00, and 1.77 for $Si_{2p}$, $C_{1s}$ and $N_{1s}$ respectively. The transmission factor (T) of the spectrometer and the electron mean free path (λ) were drawn from the relation $\lambda^* T = E_k^{0.7}$, where $E_k$ is the kinetic energy of the photoelectrons. Attenuation from the electron mean free path and from the transfer function of the spectrometer was then accounted for. The surface composition was expressed in atom percent and the typical uncertainty was 5% of the measured values for the peaks above 10 atom percent.

Density of Quaternary Ammonium Groups

The density of quaternary ammonium groups was titrated using the electrostatic interaction between negatively charged fluorescein molecules and the quaternary ammonium sites present on the polymer (Tiller J. C. et al., "Designing surfaces that kill bacteria on contact", PNAS 98, 5981-5985, 2001). The samples were first immersed in a 1% aqueous solution of fluorescein disodium salt and rinsed extensively after 10 minutes to remove the unreacted molecules. The bound molecules were then exchanged by immersing the derivatized samples in 10 ml of PBS (100 mM, pH 8) containing 25 mmol of hexadecyltrimethylammonium chloride, $C_{16}H_{36}N(CH_3)_3^+$ Cl⁻ The solution was sonicated during 15 minutes and the concentration of dye released was then measured by UV-visible spectroscopy at 501 nm, taking the value of 77000 $M^{-1}$ $cm^{-1}$ for the extinction coefficient of fluorescein.

Determination of Bactericidal Efficiency at the Microscopic Level

A technique based on epifluorescence microscopy was used in order to study the antimicrobial activity of the samples in situ. In the case of the functionalized glass surface, a 30 μL sessile droplet of a bacterial inoculum at an optical density of 0.5 (corresponding to about $5 \cdot 10^4$ cells) was deposited. In the case of the cotton fabric (weighing 50 mg), a 100 μL droplet was adsorbed in the fabric by capillarity. The solution contained also 1 to 3 μl of a mixture of two fluorescent markers (LiveDead™ stock solution diluted 1000 times in PBS, Molecular probes, Portland, Oreg., USA). The treated microscope slides were covered by a thin glass plate whereas the cotton samples were squeezed between 2 untreated glass plates. A commercial epifluorescence microscope (DMR Leica, Germany) equipped with a 100× oil immersion objective (numerical aperture 1.25) was used for the optical observations. The adsorbed bacteria appear as green dots if still viable and as red dots if their membrane has been damaged following contact with the active substrate. The images were recorded with a color CCD camera (CoolSnap, RS Photometrics, USA) and analyzed with a computer imaging system (RS image software).

III. Results and Discussion

1. Characterization of the Polymer Layer Deposited on the Solid Substrate a) Thickness The thickness of the polymer film was measured by ellipsometry after spreading drops of known volumes and concentrations on oxidized silicon wafers. It was found that it increases monotonously with the total amount of polymer deposited. The measured thicknesses were in the 10 to 50 nm range for droplet volumes between 5 and 25 μL at a concentration of 1 mg/mL. These results are not absolute since they are based on the assumption that the organic layer is compact and has a density of 1 $g \cdot cm^{-3}$. For such small thicknesses, it is actually not possible to derive independently those 2 parameters from the ellipsometric set of data. Thickness variation across the sample was in the range of 5 to 10 nm, which can be considered as relatively uniform. It was also checked by weighing that the entire polymer amount contained initially in the droplet was adsorbed on the surface after drying. It is therefore logical to observe by ellipsometry that the thickness of the polymer layer is proportional to the volume and polymer concentration of the droplet deposited on the solid substrate. We have also checked that identical results were obtained by deposition of a single drop of volume, V, or n drops of volume, V/n.

b) Density of Quaternary Ammonium Groups as a Function of the Number of Deposition Steps The density of quaternary ammonium groups present on cotton fabrics has been measured as a function of the number of drops deposited, using the fluorescein derivatization method. The drop volume was always 240 μL, and the polymer concentration was attached at 1 mg/mL. the layer thickness is expected to increase by 12 nm at each deposition. Between the measurements, the fabric was cured at a temperature of 110° C. As shown in FIG. 1 in annex, the charge density increases linearly at first, but saturates after 3 deposition steps. The initial slope corresponds to an increase of 4 charges per nm2 at each deposition step. The plateau value corresponds to a charge density of 14 positive charges per $nm^2$ (see FIG. 1). Interestingly, if one calculates the number of charged monomers per unit surface, knowing that 240 μg of polymer is deposited per step, the cotton fabric was weighing 50 mg and has an estimated specific surface area of 0.4 $m^2/g$, one finds that there are 24 charges per $nm^2$. Such value is much higher, by a factor of 6, than the experimental value. A very similar factor of 7 had been observed by Tiller for poly (4-vinyl-N-hexylpyridinium bromide) films (Tiller J. C. et al., "Designing Surfaces That Kill Bacteria On Contact", PNAS 98, 5981-5985, 2001). His assumption was that the equilibrium constant for the formation of the ammonium-fluorescein complex is such that the binding stoichiometry is 1 fluorescein per 7 quaternized monomers. It is also possible that some of the cationic sites are inaccessible for steric reasons, due to the large size of the fluorescein ion. Similar steric arguments would also explain the saturation of the charge density after 3 deposition steps. Due to a thickening of the layer or an increase in its compactness, the dye can no longer penetrate deep into the polymer layer as it gets thicker and thicker. If one assumes that the layer is close-packed and has a density of unity, each deposition step corresponds to a thickness increase of 12 nm. That would mean that the maximum layer depth that can be probed by the marker is 36 nm.

b) Chemical Characterization of the Treated Cotton by XPS

Treated cotton fabrics were examined by X-ray Photoelectron Spectroscopy. The low resolution spectra obtained in the range 0 to 1100 eV show well-defined peaks corresponding to C, O, N, Cl and Si at 285, 532, 400, 199 and 102 eV respectively. The last 3 peaks clearly result from the chemical treatment since they are not observed on the untreated samples. They have been further characterized by performing individual high resolution spectra for each particular atom. This procedure allows getting detailed information on the chemical state. The relative concentrations in atom percent for all peaks can then be extracted from the peak amplitudes, after correcting for the sensitivity factors. The data for 2 different samples are shown in Table 1.

The nitrogen peak is composed of 2 separate peaks centered at 399.8 and 402.3 eV. The first peak correspond to uncharged nitrogen and is due to remnants of the initial reactant molecule N,N dimethylbutylamine $(CH_3)_2N-(CH_2)_3-CH_3$. The second peak corresponds to the quaternary ammoniums of the fully quaternized poly-(vinylbenzyl) statistical copolymer (PVB-Si-Q). They are the sites of interest for the biocidal activity. Table 1 shows that the peak amplitude for sample 2 corresponds to 1.6 atom percent for $N^+$ and 0.6 atom percent for N. The amount of unreacted N,N dimethylbutylamine is non negligible, despite our extensive washing at the end of the reaction. The amount of quaternized ammonium relative to carbon content is 50:1. This result is noticeably smaller than the C:N ratio calculated from the polymer structure depicted in scheme 2, which is 15:1. The rationale for this difference is that the polymer layer is of nanometric thickness. XPS then probes the cellulose substrate as well as the polymer layer. Since cellulose contains no nitrogen, the ratio of C to N decreases.

The chlorine peak can be decomposed in 2 peaks centered at 197.0 and 198.9 eV, respectively, and with an amplitude ratio of 2:1. These peaks correspond to $Cl_{2p3/2}$ and $Cl_{2p1/2}$. Their energy positions indicate that chlorine is in a mineral $Cl^-$ form rather than in an organic form: for instance, the chlorine peaks of $-(CH_2)Cl$ are observed at 200 and 202 eV. Therefore the chlorine content is not attributable to residual vinylbenzylchloride monomers that have not reacted. Rather, it represents the counterions of the quaternary ammonium groups. This interpretation is well supported by the fact that $N^+$ and $Cl^-$ are in equivalent amounts according to XPS. Within experimental accuracy, stoichiometry is 1:1.

The silicon peak is due to the trimethoxysilane side groups that are the sites of interest for the grafting of the statistical copolymer on the substrates. The peak amplitude corresponds to 0.8 atom percent for sample 2. Elemental analysis on the copolymer used for this sample has determined that the fraction of units with silane side groups is 14%, therefore one expects from the copolymer structure depicted in scheme 2 that the ratio of Si:N$^+$ should be 0.14. Experimentally we find Si:N$^+$=0.5. Silicon is a well-known contaminant in laboratory environments and it is also present in our samples, which explains the high value of our Si:N$^+$. More interestingly, the Si peak position at 102 eV is in support of the formation of siloxane bonds between the statistical copolymer and the cotton substrate. Metallic Si would give a peak at 99 eV and Si in silicon dioxide would show a peak at 103.5 eV.

The last column of Table 1 compares the density of ammonium groups in the grafted polymer film measured by XPS with the density measured by UV spectroscopy in the fluorescein complexation method. Since XPS measurements are not absolute, the ratio is not necessarily unity. In our case we find that the ratio is 6.2 for sample 1 and 5.9 for sample 2. Within experimental accuracy, we can consider these 2 values to be identical. That proves that the 2 methods of detection are consistent with each other. When UV spectroscopy detects a higher amount of ammonium groups (as in sample 2 compared to sample 1), the XPS signal is also larger, and with the correct factor of proportionality (factor of 3 between sample 2 and sample 1).

TABLE 1

| | N$^+$ from UV | Chemical surface composition (atom per cent) | | | | | | Ratio of N$^+_{(XPS)}$/ N$^+_{(UV)}$ |
|---|---|---|---|---|---|---|---|---|
| | (mol/nm$^2$) | C | O | N | N$^+$ | Cl | Si | |
| Sample 1 | 3.4 | 77.06 | 20.39 | 0.88 | 0.55 | 0.42 | 1.26 | 6.1 |
| Sample 2 | 9.6 | 80.07 | 15.40 | 2.23 | 1.62 | 1.50 | 0.82 | 5.9 |

2. Bactericidal Effect of Charged Surfaces

Pictures were taken corresponding to a series of optical microscopy observations of *E. coli* bacteria adsorbed on cotton fibers. Individual fibers can clearly be seen and they give the scale of the image since their diameter is of the order of 10 μm. Bacteria appears as bright dots of micron size. On one of the images, the fibers have not been treated and it is noticed that very few bacteria are adsorbed. On another image, numerous bacteria are adsorbed on the fibers, evidencing a strong electrostatic attraction between the positively charged substrate and the negatively charged bacteria. If the bacteria have been previously labeled with a fluorescent marker of viability (Live and Dead, from Molecular Probes) they appear green, evidencing that they are in their normal, living, state. The color does not change even after several hours (220 minutes for this particular image). The bacteria are well individualized, with a regular shape and sharp margins. It can therefore be said that they remain perfectly viable and that their overall aspect has not been changed, following adsorption on this treated fiber.

The situation is very different on another third image. In that case, the fibers have been treated with the statistical copolymer of example 1 in such a way that the charge density of quaternary ammonium is 9 mol/nm$^2$. This is 3 times higher than in the previous picture. The bacteria are no longer distinguishable and the fibres are surrounded by a diffuse cloud of material of red color. The fiber has evidently destroyed the bacteria that were adherent on it. The action of the fiber, however, is very local. Bacteria that have not been adsorbed and are still in solution remain green. The picture was taken after 2 hours of contact. The cloud is formed by material initially contained within the bacteria. Pictures taken at shorter times show that the bacteria becomes red after about 10 minutes but still keep their regular shape. It is only with the course of time that they lose their distinctive cylindrical shape and their margins become blurred.

Similar effects were observed on treated glass slides. Bacteria remain alive if the charge density is 3 mol/nm$^2$ but die in a matter of tens of minutes if the charge density is 12 mol/nm$^2$.

To conclude, these experiments show that the statistical copolymer can modify the surface of solid substrates containing labile hydrogen atoms such as glass slide and cotton fibers in a way that the substrate become cytotoxic for bacteria that comes in contact with it.

EXAMPLE 3

Synthesis of a Statistical Copolymer via a Radical Copolymerization

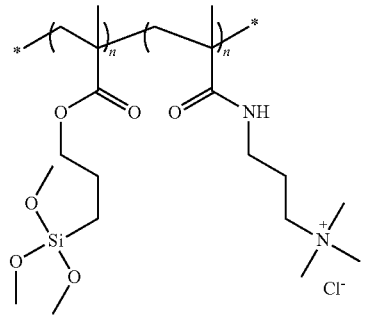

Synthesis of the copolymer comprising 3-(trimethoxysilyl)propyyl methacrylate (TMSA) and [3-(Methacryloylamino)propyl]trimethylammonium chloride (MPTA). Prior to polymerization, MPTA in solution in water was extracted with ethyl acetate to remove the inhibitor before evaporation to dryness. TMSA (1 g, 4.53 mmol), MPTA (108 μL, 0.45 mmol), and AIBN (20 mg) were placed in a vial and dissolved in MeOH (60 mL). The mixture was degassed using Ar stream. The reaction carried out at 70° C. for 24 h. After evaporation and precipitation with diethyl ether, the polymer was obtained as a white foam.

$^1$H NMR (300 MHz, D$_2$O)=0.8-1.2 (m), 1.72 (bs), 1.8-2.1 (s), 3.09 (s), 3.31 (s), 3.55 (s), 4.01 (bs)

The invention claimed is:

1. A method for treating at least a surface of a substrate containing labile hydrogen atoms to confer cytotoxic properties or cell-adhesion properties, the method comprising exposing, within a liquid medium, said substrate or a surface thereof with at least a copolymer, said copolymer containing at least a monomer unit of type A including at least a reactive site able to attach to said substrate or said surface by covalent bonds and at least a monomer unit of type B including at least one molecule able to confer antimicrobial, antiviricidal and/ or antifungicidal or cell-adhesion properties to said substrate or said surface, said step being carried out in efficient conditions to promote the covalent grafting of said copolymer to said substrate or a surface thereof, and wherein: the reactive site for promoting the attachment of said copolymer to a substrate is included in monomer of type A under the following formula

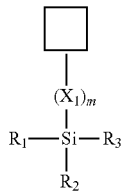

wherein
□ means the link to monomer A
m is 0 or 1,
$X_1$ represents an amine, an amide or a ketone function, an oligoethylene glycol, an arylene group, a $(C_1-C_6)$alkylarylene, or a $(C_1-C_8)$alkylene which may be interrupted by any one of an amine, an amide or a ketone function, one of the carbon atom in the $(C_1-C_8)$alkylene being optionally replaced by a quaternary ammonium, a quaternary phosphonium a $(C_1-C_4)$alkylpyridinium, a $(C_1-C_4)$alkylimidazolium or a guanidinium group, at least one of $R_1$, $R_2$ and $R_3$ is able to react with an hydroxyl, a thiol or an amine group, and the other one or two radicals chosen among $R_1$, $R_2$ and $R_3$ independently represent a $(C_1-C_4)$alkoxy, or any one of the group $R_1$, $R_2$ and $R_3$ is a group showing a
character of leaving group or alternatively

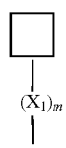

represents a part of monomer unit containing a 5- or 6-membered saturated ring containing a quaternary ammonium.

2. The method according to claim 1, wherein the copolymer is a statistical copolymer.

3. The method according to claim 1, wherein the monomer unit of type B comprises a quaternary ammonium group, a quaternary phosphonium group, a guanidinium group or an aminopenicillanic acid.

4. The method according to claim 1, wherein the copolymer comprises a polymeric chain backbone selected from the group consisting of polyethylene, polyacrylamide, polystyrene, polyvinylalcohol, polyallylamine, polyallylalcohol, polyvinylbenzyl, polyamine, polymethacrylate, polyether, poly(ethylene-alt-succinimide) and poly(diallyldimethylammonium).

5. The method according to claim 1, wherein the molecule able to confer antimicrobial, antiviridcidal and/or antifungicidal or cell-adhesion properties is included in the monomer of type B under the following formula:

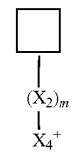

wherein
□ means the link to monomer B
m is 0 or 1,
$X_2$ represents an amine, an amide, an ester or a ketone function, an oligoethylene glycol, an arylene group, a $(C_1-C_6)$alkylarylene, or a $(C_1-C_8)$alkylene which may be interrupted by anyone of an amine, an amide or a ketone function, and
$X_4^+$ represents:
a trialkylammonium of formula

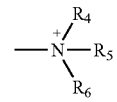

wherein $R_4$, $R_5$ and $R_6$ independently represent a $(C_1-C_{12})$alkyl, hydroxy$(C_1-C_{12})$alkyl or fluoro$(C_1-C_{12})$alkyl group,
a trialkylphosphonium of formula

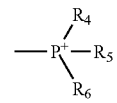

wherein $R_4$, $R_5$ and $R_6$ are such as defined above,
a $(C_1-C_4)$alkylpyridinium group of formula:

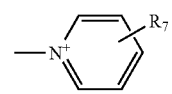

wherein $R_7$ represents a $(C_1-C_4)$alkyl,
a $(C_1-C_4)$alkylimidazolium group of formula:

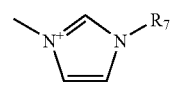

wherein $R_7$ is as described above,
a guanidinium group of formula

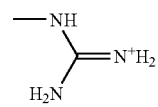

a trialkylphosphonium of formula

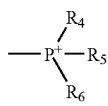

wherein $R_4$, $R_5$ and $R_6$ are such as defined above, or alternatively

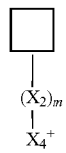

represents a monomer unit containing a 5- or 6-membered saturated ring containing a quaternary ammonium.

6. The method according to claim 1, wherein the monomer unit of type B is represented by the compound of formula (II)

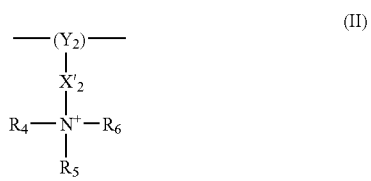

wherein $R_4$, $R_5$ and $R_6$ independently represent a $(C_1-C_6)$alkyl, a hydroxyl$(C_1-C_6)$alkyl or a fluoro$(C_1-C_6)$alkyl, $X'_2$ represents an $(C_1-C_4)$alkylene, an oligoethylene glycol or an arylene group, $Y_2$ is a part of the polymeric chain backbone and is an ethylene optionally substituted by a methyl group, an acrylamide, an ethyleneimine, a methylmethacrylate or a propylene glycol.

7. The method according to claim 1, wherein the monomer unit of type A is represented by the compound of formula (I)

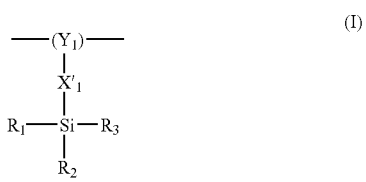

wherein at least one of $R_1$, $R_2$ and $R_3$ is able to react with an hydroxyl, a thiol or an amine group, $X'_1$ represents an arylene group, a $(C_1-C_6)$alkylarytene group or a $(C_1-C_8)$ alkylene group, optionally one of the carbon atom in the alkylene group being replaced by an atom selected from the group consisting of a nitrogen atom, a quaternary phosphonium, an alkylpyridinium, an alkylimidazolinium, and a guanidinium group, $Y_1$ is a part of the polymeric chain backbone is an ethylene optionally substituted by a methyl group, an acrylamide, an ethyleneimine, a methylmethacrylate group or a propylene glycol.

8. The method according to claim 1, wherein the monomer unit of type A contains at least a trialkoxysilane group.

9. The method according to claim 1, wherein at least one of $R_1$, $R_2$ and $R_3$ is a halogen atom, a hydroxyl group, a halogeno $(C_1-C_{10})$alkyl, or a $(C_1-C_{10})$alkoxy group.

10. The method according to claim 2, wherein a percentage of monomer unit of type A and monomer unit of type B based on the average total number of monomers of the copolymer is adjusted to ensure the hydrosolubility of the statistical copolymer.

11. The method according to claim 10, wherein a percentage of monomer unit of type A out of the total amount of monomer units is between 1% to 50%, whereas a percentage of monomer of type B out of the total amount of monomer units is between 50% to 99%.

12. The method according to claim 10, wherein the water-soluble statistical copolymer shows a molecular weight ranging between $10^3$ and $10^6$ g/mol.

13. The method according to claim 1, wherein exposing, within a liquid medium, said substrate or said surface with at least a statistical copolymer is followed by drying.

14. The method according to claim 1, wherein the liquid medium is an aqueous medium.

15. A cytotoxic or cell-adhesion statistical copolymer containing at least a monomer unit of type A and at least a monomer unit of type B, wherein monomer unit of type A contains at least a reactive site able to attach to a substrate or a surface containing labile hydrogen atoms by covalent bonds, wherein: the monomer unit of type B contains at least one molecule able to confer antimicrobial, antiviricidal and/or antifungicidal properties or cell-adhesion properties to said substrate or said surface, and the reactive site for promoting the attachment of said copolymer to a substrate is included in monomer of type A under the following formula

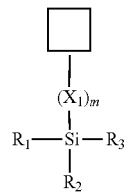

wherein

□ means the link to monomer A m is 0 or 1, $X_1$ represents an amine, an amide or a ketone function, an oligoethylene glycol, an arylene group, a $(C_1-C_6)$alkylarylene, or a $(C_1-C_8)$alkylene which may be interrupted by any one of an amine, an amide or a ketone function, one of the carbon atom in the $(C_1-C_8)$alkylene being optionally replaced by a quaternary ammonium, a quaternary phosphonium a $(C_1-C_4)$alkylpyridinium, a $(C_1-C_4)$alkylimidazolium or a guanidinium group, at least one of $R_1$, $R_2$ and $R_3$ is able to react with an hydroxyl, a thiol or an amine group, and the other one or two radicals chosen among $R_1$, $R_2$ and $R_3$ independently represent a $(C_1-C_4)$alkoxy, or any one of the group $R_1$, $R_2$ and $R_3$ is a group showing a character of leaving group or alternatively

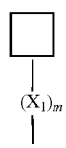

represents a part of monomer unit containing a 5- or 6-membered saturated ring containing a quaternary ammonium.

16. A cytotoxic or cell-adhesion statistical copolymer containing at least a monomer unit of type A and at least a monomer unit of type B, the monomer of unit type B comprising a quaternary ammonium group, a quaternary phosphonium group, a guanidinium group, or an aminopenicillanic acid, wherein: the monomer unit of type A contains at least a reactive site able to attach to a substrate or a surface containing labile hydrogen atoms by covalent bonds and in that monomer unit of type B contains at least one molecule able to confer antimicrobial, antiviricidal and/or antifungicidal properties or cell-adhesion properties to said substrate or said surface, and the reactive site for promoting the attachment of said copolymer to a substrate is included in monomer of type A under the following formula

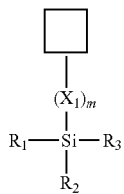

wherein
☐ means the link to monomer A
m is 0 or 1,
$X_1$ represents an amine, an amide or a ketone function, an oligoethylene glycol, an arylene group, a $(C_1-C_6)$alkylarylene, or a $(C_1-C_8)$alkylene which may be interrupted by any one of an amine, an amide or a ketone function, one of the carbon atom in the $(C_1-C_8)$alkylene being optionally replaced by a quaternary ammonium, a quaternary phosphonium a $(C_1-C_4)$alkylpyridinium, a $(C_1-C_4)$alkylimidazolium or a guanidinium group,
at least one of $R_1$, $R_2$ and $R_3$ is able to react with an hydroxyl, a thiol or an amine group, and the other one or two radicals chosen among $R_1$, $R_2$ and $R_3$ independently represent a $(C_1-C_4)$alkoxy, or any one of the group $R_1$, $R_2$ and $R_3$ is a group showing a character of leaving group or alternatively

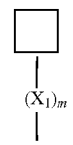

represents a part of monomer unit containing a 5- or 6-membered saturated ring containing a quaternary ammonium.

17. A composition for treating at least a surface of a substrate containing labile hydrogen atoms, the composition comprising a cytotoxic statistical copolymer according to claim 15.

18. A substrate provided with antibiotic, bactericidal, viricidal and/or fungicidal properties or cell-adhesion properties, wherein at least one surface of the substrate is obtainable by the method according to claim 1.

19. The substrate according to claim 18, wherein the substrate is selected from the group consisting of glass, metals and metal oxides, plastics, wood, paper, leather, textiles, jute, linen, hemp, wool, animals' hair, silk, and synthetic fabrics.

20. The substrate according to claim 18, wherein a density of active antibiotic site per unit surface area ranges from $10^{14}$ to $10^{16}$ per cm$^2$.

* * * * *